(12) United States Patent
Jung et al.

(10) Patent No.: US 8,211,441 B2
(45) Date of Patent: Jul. 3, 2012

(54) USE OF *L. UNDULATA* EXTRACT AS THERAPEUTICS FOR ALLERGIC DISEASES

(75) Inventors: Won-Kyo Jung, Gwangju (KR); Il-Whan Choi, Busan (KR); Se-Kwon Kim, Busan (KR); Sung Su Yea, Busan (KR); Yung Hyun Choi, Busan (KR); Inhak Choi, Busan (KR)

(73) Assignee: Pukyong National University Industry-Academic Cooperation, Busan (KR)

( * ) Notice: Subject to any disclaimer, the term of this patent is extended or adjusted under 35 U.S.C. 154(b) by 0 days.

(21) Appl. No.: 13/170,594

(22) Filed: Jun. 28, 2011

(65) Prior Publication Data

US 2011/0256171 A1  Oct. 20, 2011

Related U.S. Application Data

(62) Division of application No. 12/323,280, filed on Nov. 25, 2008, now Pat. No. 7,993,653.

(51) Int. Cl.
*A61K 36/00* (2006.01)
*A61K 36/02* (2006.01)

(52) U.S. Cl. .................... 424/195.17; 424/725; 514/855

(58) Field of Classification Search ........................ None
See application file for complete search history.

*Primary Examiner* — Qiuwen Mi
(74) *Attorney, Agent, or Firm* — Dickinson Wright PLLC

(57) ABSTRACT

The present invention relates to a method of preventing or treating allergic diseases such as allergic rhinitis, atopic dermatitis, anaphylaxis, and asthma, which comprises administering an extract of *Laurencia undulata* in a therapeutically effective amount to a patient in need thereof.

16 Claims, 5 Drawing Sheets

USE OF *L. UNDULATA* EXTRACT AS THERAPEUTICS FOR ALLERGIC DISEASES

CROSS REFERENCE TO A PARENT APPLICATION

The present application is a divisional application of application Ser. No. 12/323,280 filed on Nov. 25, 2008 now U.S. Pat. No. 7,993,653, the contents of which are incorporated herein by reference.

FIELD OF THE INVENTION

The present invention relates to a method of preventing or treating allergic diseases such as allergic rhinitis, atopic dermatitis, anaphylaxis, and asthma, which comprises administering an extract of *Laurencia undulata* in a therapeutically effective amount to a patient in need thereof.

BACKGROUND OF THE INVENTION

Among various allergic diseases, especially, asthma is a complex inflammatory disease of the lung characterized by variable airflow obstruction, airway hyperresponsiveness, and airway inflammation. The inflammatory response in the asthmatic lung is characterized by infiltration of the airway wall by mast cells, lymphocytes and eosinophils and is associated with the increased expression of several inflammatory proteins, including cytokines, enzymes, and adhesion molecules in the airways. The T helper 2 (Th2)-type cytokines such as interleukins (IL)-4, IL-5, and IL-13, which are produced by activated $CD4^+$ T cells play a central role in the pathogenesis of asthma by controlling the key process of immunoglobulin E (IgE) production, the growth of mast cells and the differentiation and activation of mast cells and eosinophils. The direction of Th cell differentiation is determined by the cytokine environment at the site of initial antigenic activation. It has been well documented that the presence of IL-4 during the induction phase accounts for a predominance of Th2 cells, which subsequently determine the allergic inflammatory responses. Th2 cells are the predominant lymphocyte population that infiltrates the airways of asthmatics, and the cytokine products of Th2 cells perform essential roles in airway eosinophilia, airway hyperresponsiveness, and serum IgE in animal models.

Meanwhile, marine algae have been consumed in Asia since ancient times, which are rich in vitamins, minerals, dietary fibers, proteins, polysaccharides, etc. Moreover, seaweeds are considered to be a rich source of antioxidant. Hence, many types of seaweed have been examined to identify new and effective antioxidant compounds, as well as to elucidate the mechanisms of cell proliferation, anti-inflammation and apoptosis (Yuan, Y. V. et al., 2006, Antioxidant and antiproliferative activities of extracts from a variety of edible seaweeds, Food and Chemical Toxicology 44, 1144-1150; Heo, S. J. et al., 2006, Antioxidant activities of red algae from Jeju island, Algae 21, 149-156; Nahas, R. et al., 2007, Radical-scavenging activity of Aegean Sea marine algae, Food Chem. 102, 577-581; Kim, S. K. et al., 2008, Effects of Ecklonia cava ethanolic extracts on airway hyperresponsiveness and inflammation in a murine asthma model: Role of suppressor of cytokine signaling, Biomed. Pharmacother. 62, 289-296).

The red algal genus *Laurencia* has been known to contain natural bioactive materials of polysaccharides, polyphenols, terpenes and the other halogenated secondary metabolites. It has been reported that the red algal genus *Laurencia* possesses antioxidant, anticancer and antibacterial activities (Liang, H. et al., 2007, Effect of ethanol extract of alga *Laurencia* supplementation on DNA oxidation and alkylation damage in mice, Asia Pac J. Clin. Nutr. 16, 164-168; Pec, M. K. et al., 1999, Growth inhibition by dehydrothyrsiferol—a non-Pgp modulator, derived from a marine red alga—in human breast cancer cell lines, Int. J. Oncol. 14, 739-743; Vairappan, C. S. et al., 2001, Antibacterial halogenated metabolites from the Malaysian *Laurencia* species, Phytochemistry 58, 291-297). However, the anti-allergic activity of *L. undulate*, especially anti-asthmatic activity thereof has never been reported.

As a result of their intensive investigation, the present inventors have discovered that an extract of *Laurencia undulate* containing a large amount of polyphenols has potent anti-allergic and anti-asthmatic effects.

SUMMARY OF THE INVENTION

The object of the present invention is to provide a method of preventing or treating allergic diseases effectively without toxicity by using an extract of an edible red alga.

The constitutions of the present invention for accomplishing the above object of the present invention are as follows.

The present invention provides a method of preventing or treating allergic diseases, which comprises administering an extract of *Laurencia undulata* in a therapeutically effective amount to a patient in need thereof.

In one aspect of the present invention, there is provided an extract of *Laurencia undulata* extracted with an alcohol solution of 40% to 99%, preferably 95% ethanol.

In yet another aspect of the present invention, the extract of *Laurencia undulata* is prepared by lyophilizing and homogenizing *Laurencia undulata* followed by extracting with 95% ethanol in a weight/volume ratio of 1:10.

In still yet another aspect of the present invention, the allergic diseases are selected from the group consisting of allergic rhinitis, atopic dermatitis, anaphylaxis, and asthma.

In still yet another aspect of the present invention, the preferable allergic disease is asthma, which is caused by the increase in the levels of eosinophil, IL-4, IL-5 and TNF-α in the bronchoalveolar lavage fluid, the increase in the concentration of serum IgE, and airway hyperresponsiveness.

The present invention will now be discussed in more detail as hereunder.

*Laurencia undulata*, which is used in this invention, may be used as an extract with water, an organic solvent such as alcohol (methanol, ethanol, propanol, butanol, etc.), acetone, ethyl acetate, chloroform, dichloromethane, dioxane or ether, or an aqueous organic solvent. The extraction solvent and extraction method may be freely selected and established. The extract thus obtained may be used as it is, after concentration, or dried beforehand.

For the present invention, it is preferred to extract *Laurencia undulata* with an alcohol solution of 40 to 99%, more preferably, 95% ethanol.

For example, fresh *L. undulata* is washed with water to remove salts, epiphytes and sand attached to the surface thereof, and lyophilized and homogenized using a grinder. And then, the dried *L. undulata* powder is extracted with 95% ethanol. The ratio of the extraction solvent to the dried powder may be 1:5 w/v to 1:20 w/v. The extraction may be carried out at a temperature of 15 to 25° C., preferably at a temperature of 20° C., for several days, preferably for 3 days.

The inventive extract of *L. undulata* may be administered without particular limitation in ordinary oral dosage forms such as extracts, solutions, syrups, tablets, capsules, granules, powders, pills, and suspensions. Furthermore, it can be administered transmucosally as suppositories, inhalants or nasal drops. Those dosage forms may contain, in addition to the extract of *Laurencia undulata* as an active ingredient, the excipient, diluent, carrier and/or other additives which are commonly used in the pharmaceutical field.

The effective prophylactic or therapeutic amount of the extract of *Laurencia undulata* is dependent on the patient's clinical condition, age, body weight, etc., but the daily dose for adult is approximately 0.1 g~100 g, preferably, 1 g~50 g, more preferably 3 g~10 g, which can be administered either in a single dose or in two or more divided doses a day.

The allergic diseases which can be prevented or treated with the inventive extract of *L. undulata* include allergic rhinitis, atopic dermatitis, anaphylaxis, and asthma.

Especially, the extract of *Laurencia undulata* according to the present invention is useful for treating asthma by inhibiting airway hyperresponsiveness and inflammation, more specifically, by decreasing the levels of eosinophil, IL-4, IL-5 and TNF-α in the bronchoalveolar lavage fluid, and the concentration of serum IgE.

BRIEF DESCRIPTION OF THE DRAWINGS

The above objects and features of the present invention will become more apparent from the following description of the preferred embodiments given in conjunction with the accompanying drawings, in which.

DETAILED DESCRIPTIONS OF THE PREFERRED EMBODIMENTS

Figure 1:
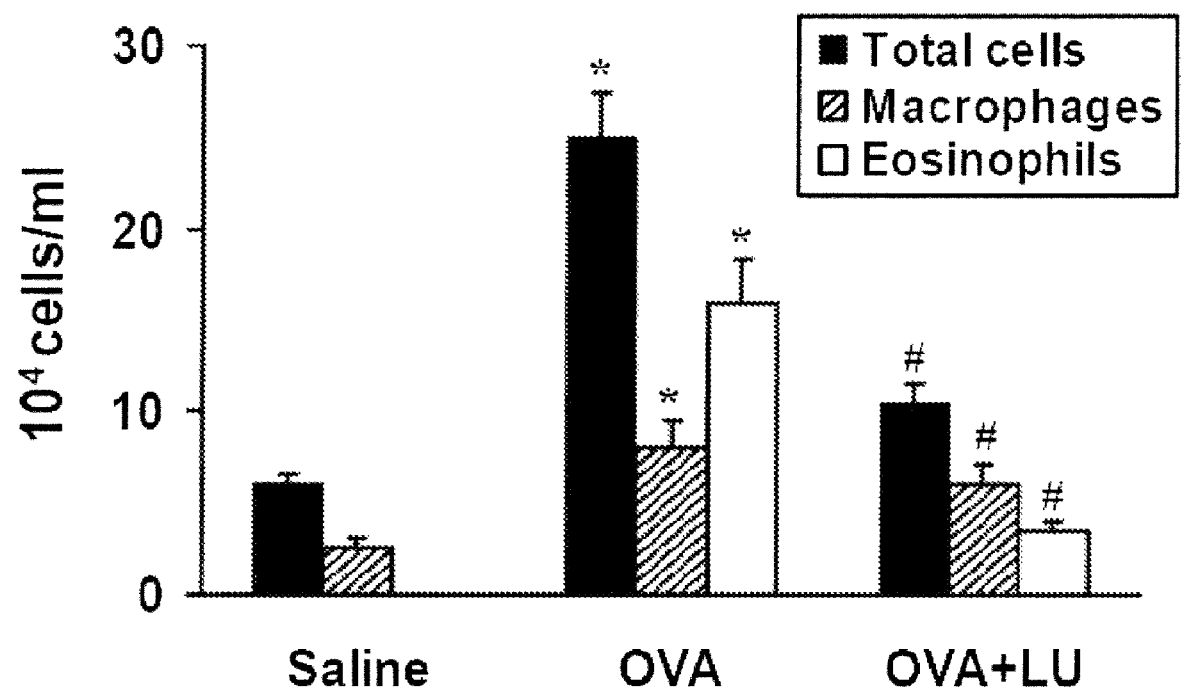
FIG. 1 illustrates the effect of an *L. undulata* extract (LU) on the recruitment of inflammatory cells into BAL in OVA-induced allergic asthmatic mice.

In the following detailed description, reference is made to the accompanying drawings that show, by way of illustration, specific embodiments in which the present invention may be practiced. These embodiments are described in sufficient detail to enable those skilled in the art to practice the present invention. It is to be understood that the various embodiments of the present invention, although different from one another, are not necessarily mutually exclusive. For example, a particular feature, structure, or characteristic described herein in connection with one embodiment may be implemented within other embodiments without departing from the spirit and scope of the present invention. The following detailed description is, therefore, not to be taken in a limiting sense, and the scope of the present invention is defined only by the appended claims, appropriately interpreted, along with the full range of equivalents to which the claims are entitled.

Airway allergen challenge causes cellular inflammation in the airway, which is dominated by eosinophils. It has been suggested that eosinophils contribute to several clinical features of allergic asthma, including tissue damage and airway hyperresponsiveness (Lotvall, J. et al., 1998, Measurement of airway hyperresponsivenes, New considerations, Thorax 53, 419-424). OVA sensitization and challenge remarkably increases the number of inflammatory cells containing eosinophils and macrophages in the BAL fluid compared to the control group. Pathological processes that result in lung eosinophilia may involve antigen-induced T cell activation through macrophages or other antigen presenting cells, the release of T cell cytokines, specific sensitization of mast cells, and the release of activating mediators by macrophages (Drazen, J. M. et al., 1996, Sorting out the cytokines of asthma, J. Exp. Med. 183, 1-5).

Initiation of allergic response appears to occur with presentation of the allergen by antigen-presenting cells to $CD^+$ T cells. Antigen-activated $CD4^+$ T cells have been shown to induce many characteristic features of asthma, including the secretion of cytokines such as IL-4 and IL-5, which regulate mucus production, inflammation, and adhesion molecules. It has been established that the inhibition of the Th2 cytokines may be useful in the treatment of allergic asthma since T cells from the lungs of asthmatics express a Th2 pattern of cytokines. Also, TNF-α plays an important role in the pathogenesis of asthma. The levels of TNF-α mRNA and protein are increased in the sputum or serum of asthmatic patients and TNF-α induces the aggravation of airway hyperresponsiveness as well as the recruitment of inflammatory cells into the airways.

Meanwhile, the level of IgE is dependent upon IL-4, IL-5, IL-13 and may be considered as an additional index of Th2 cytokine secretion in the pathogenesis of asthma. Cross-linking of allergen-specific IgE on the mast cell surface upon allergen challenge is an important key to initiate the early asthmatic reaction. Therefore, a novel therapeutic approach to asthma and other allergic diseases involves the interference in the action of IgE.

Based on the above, the present invention provides experimental evidence demonstrating that a kind of red alga, *L. undulata* extract containing a large amount of polyphenols could inhibit OVA-induced airway hyperresponsiveness and inflammation in a murine model of asthma. The administration of an *L. undulata* extract before the airway OVA challenge resulted in a significant inhibition of all asthmatic reactions. In addition, the results also suggest that an *L. undulata* extract can be effective in the treatment of other allergic diseases such as allergic rhinitis, atopic dermatitis, anaphylaxis, and asthma.

EXAMPLE 1

Preparation and Chemical Analysis of *L. undulata* Extracts

*L. undulata* extracts (hereinafter, "LU") were prepared according to the method of Heo et al. (Heo, S. J. et al., 2006, Antioxidant activities of red algae from Jeju island. Algae 21, 149-156). The red seaweed, *L. undulata* was collected along Jeju Island coast of Korea during the period from October 2005 to February 2006. Fresh *L. undulata* was washed three times with tap water to remove salts, epiphytes and sand attached to the surface thereof and stored at −20° C. The frozen samples were lyophilized and homogenized using a grinder before extraction. The dried *L. undulata* powder (1 kg) was extracted with 95% EtOH (1:10 w/v) at 20° C. for 3 days and evaporated in vacuo. The concentrated LU was freshly dissolved in DMSO before use.

Phenolic contents of LU were determined by the method of Shetty et al. (Shetty, K. et al., 1995, Prevention of vitrification associated with the in vitro shoot culture of oregano (*Origanum vulgare*) by *Pseudomonas* spp. J. Plant Physiol. 147, 447-451). 1 ml of the extract, 1 ml of 95% EtOH, 5 ml of distilled water, and 0.5 ml of 50% Folin-Ciocalteu reagent (Sigma Chemical, St. Louis, Mo.) were mixed. The mixture was allowed to react for 5 min, 1 ml of 5% $Na_2CO_3$ was added thereto, and then, the resulting mixture was placed in the dark for 1 h. Absorbance was measured at 725 nm and gallic acid standard curve was obtained for the calibration of phenolic content.

Total carbohydrate was measured by the phenol-sulfuric acid method of Dubois et al. (Dubois, M. et al., 1956, Colorimetric method for determination of sugars and related substances, Anal. Chem. 28, 350-356) using a mixture of galactose and fucose (1:1 weight ratio) as a standard. The sulfate content in the total carbohydrate of LU was measured by the $BaCl_2$/gelation method (Saito, H. et al., 1968, Enzymatic methods for the determination of small quantities of isomeric Chondroitin Sulfates, J. Biol. Chem. 243, 1536-1542).

The yield of LU was 8.9% (% dry wt. of alga). In the chemical analysis, total phenolic content of LU was determined as 43.6±0.3 mg/g (n=3). However, a low amount of carbohydrate (1.2±0.1 mg/g, n=3) was detected in LU. The sulfate content of LU was determined as 0.07 (sulfate/total sugar).

EXAMPLE 2

In Vivo Study for Anti-Allergic and Anti-Asthmatic Effects of *L. undulata* Extracts Female C57BL/6 mice were obtained from the Charles River Laboratories (Yokohama, Japan), and were kept in an animal facility for at least 1 week before use. All mice were at 6-8 weeks of age.

In the control group, mice were exposed to aerosolized saline. Aerosolization was performed for 20 min by placing the mice in a chamber (15×25×15 cm) connected to the ultrasonic nebulizer (NE-U12, Omron, Tokyo, Japan).

In the test group, mice were immunized on days 1 and by intraperitoneal injection of 20 μg ovalbumin (OVA) emulsified in 1.0 mg aluminium hydroxide adjuvant in a total volume of 200 μl. Mice were challenged via the airway with OVA (50 mg/ml of saline) each day from days 22 to 24 on consecutive days. In the LU-treated group, mice were injected intraperitoneally with 20 mg/kg/day in 200 μl of *L. undulata* extract each day from days 16 to 20 on consecutive days.

In the following experiments, data are expressed as means±S.E.M. Student's t-test was used to analyse data between the groups and analysis of variance (ANOVA) among groups followed by Dunnet's t-testfor multiple comparisons. The statistical significance was set at P<0.05.

The Effect of LU on Cellular Changes in BAL Fluid 2 days after the last OVA challenge, the mice were sacrificed with a lethal dose of phenobarbital, and the tracheas of mice were cannulated while gently massaging the throax. Lungs were lavaged with 0.7 ml of PBS. The BAL fluid samples were collected and the number of cells in a 50 μl aliquot was determined using a hemocytometer. The remaining samples were centrifuged, and the supernatants were stored at −70° until the assay of cytokines. The pellet was resuspended in PBS and cytospin preparations of BAL cells were stained with Diff-Quik (International reagents Corp., Kobe, Japan). Two independent, blinded investigators counted the cells using a microscope. Approximately 400 cells were counted in each of four different random locations. Results were recorded as mean±S.E.M. from five separate experiments (n=6 per group).

As shown in FIG. 1, the number of eosinophils occupied 60% more of the total cells in the BAL fluid. 2 days after the OVA challenge, the number of eosinophils in the BAL fluid was increased to about 16-fold, compared to that in the control group. Interestingly, the number of eosinophils observed in the LU-treated group was decreased to 0.22-fold, compared to that in the OVA-challenge group (*p<0.05 vs. saline-treated mice; #p<0.05 vs. OVA-treated mice).

The Effect of LU on the Pathological Changes in Lung Tissues

In this experiment, six animals were assigned to each group. 48 h after the last challenge, lungs were removed from the mice after they had been sacrificed. Prior to the removal of the lungs, the lungs and tracheas were filled intratracheally with a fixative (4% paraformaldehyde) using a ligature around the trachea. Lung tissues were fixed with 10% (v/v) paraformaldehyde. The specimens were dehydrated and embedded in paraffin. For histological examination, 4 μm sections of the fixed embedded tissues were cut on a Leica model 2165 rotary microtome (Leica, Nussloch, Germany), placed on glass slides, deparaffinized, and sequentially stained with hematoxylin 2 and eosin-Y (Richard-Allan Scientific, Kalamazoo, Mich.). An inflammation score was graded by three independent investigators who were not associated with this study.

Figure 2:
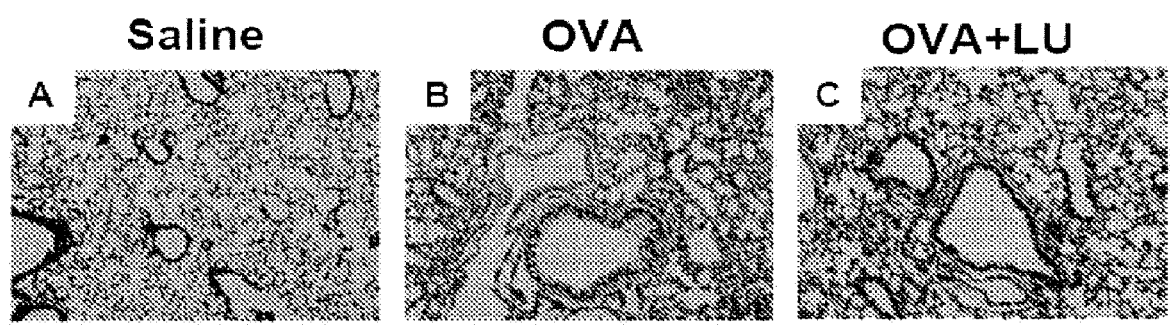
FIG. 2 shows the inhibitory effect of an *L. undulata* extract (LU) on pathological changes in lung tissues of OVA-sensitized and OVA-challenged mice.

The results of histological examination of the lung tissues paralleled the cell numbers in the BAL fluids (X200, FIG. 2). A marked influxe of inflammatory cells into the airway and around the blood vessels was observed in the OVA-sensitized/challenged mice, but not in the saline-treated control mice. Mice treated with LU showed a marked reduction in the infiltration of inflammatory cells in the peribronchiolar and perivascular regions. Mucus hypersecretion and the occlusion of the airways were the prominent histopathologic features of the murine asthmatic lung. Mucus cell hypertrophy and airway luminal narrowing caused by secreted mucus were observed in the OVA-sensitized/challenged mice. Administration of LU resulted in a marked improvement of luminal narrowing in the airway. These results suggest that LU is highly capable of inhibiting the development of allergic status induced by OVA in mice.

The Effect of LU on the Level of Cytokines in the BAL Fluid

To determine if pretreatment with LU affects the secretion of cytokines in the BAL fluid, the levels of cytokines in the BAL fluid were determined by enzyme-linked immunosorbent assay (ELISA). BAL fluids were obtained 4 h after the last airway challenge. ELISA kits from R&D Systems (Minneapolis, Minn.) were employed for the measurement of IL-4, IL-5, and TNF-α. Results were recorded as mean±S.E.M from five separate experiments (n=6 per group).

Figure 3:
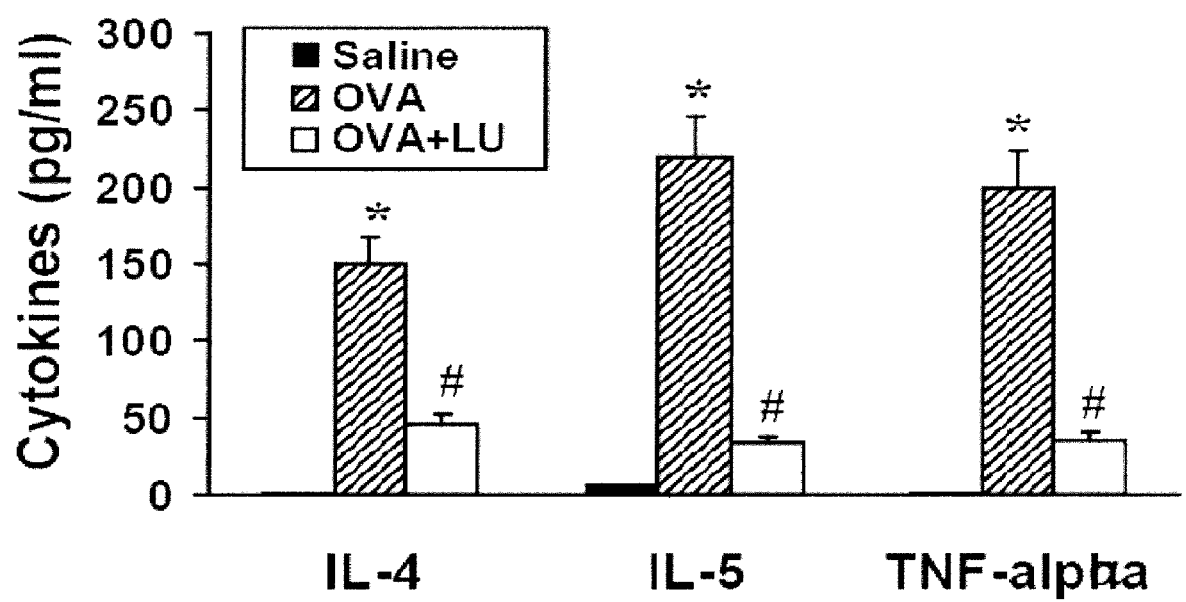
FIG. 3 presents the effect of an *L. undulata* extract (LU) on the levels of IL-4, IL-5, and TNF-α.

As illustrated in FIG. 3, the levels of IL-4, IL-5, and TNF-α in the BAL fluid were significantly increased by airway challenge with OVA when compared to those of the control group. The administration of LU reduced the concentration of IL-4 and IL-5 by 70% and 85%, respectively, and led to an 83.5% reduction in TNF-α secretion (*p<0.05 vs. saline-treated mice; # p<0.05 vs. OVA-treated mice). It has been suggested that LU has inhibitory activities on $CD4^+$ T cells and eosinophils involved in asthmatic inflammation.

The Effect of LU on the Airway Hyperresponsiveness

Airway hyperresponsiveness was measured 3 days after the last OVA challenge in an unrestrained conscious state.

Mice were placed in a barometric plethysmographic chamber (All Medicus Co., Seoul, Korea) and baseline readings were taken and averaged for 3 min. Aerosolized methacholine (Mch) of from 2.5 to 50 mg/ml was then nebulized through an inlet of the main chamber for 3 min, readings were taken and were averaged for 3 min after each nebulization. The bronchopulmonary resistance was expressed as enhanced pause (Penh), calculated as: [expiratory time (Te)/relaxation time (RT)−1]×[peak expiratory flow (PEF)/peak inspiratory flow (PIF)], according to the manufacturer's protocol. Results were expressed as the percentage of the increase in Penh following challenge with each concentration of Mch, where the baseline Penh (after saline challenge) is expressed as 100%. Results were also recorded as mean±S.E.M. from five separate experiments (n=6 per group).

Figure 4:
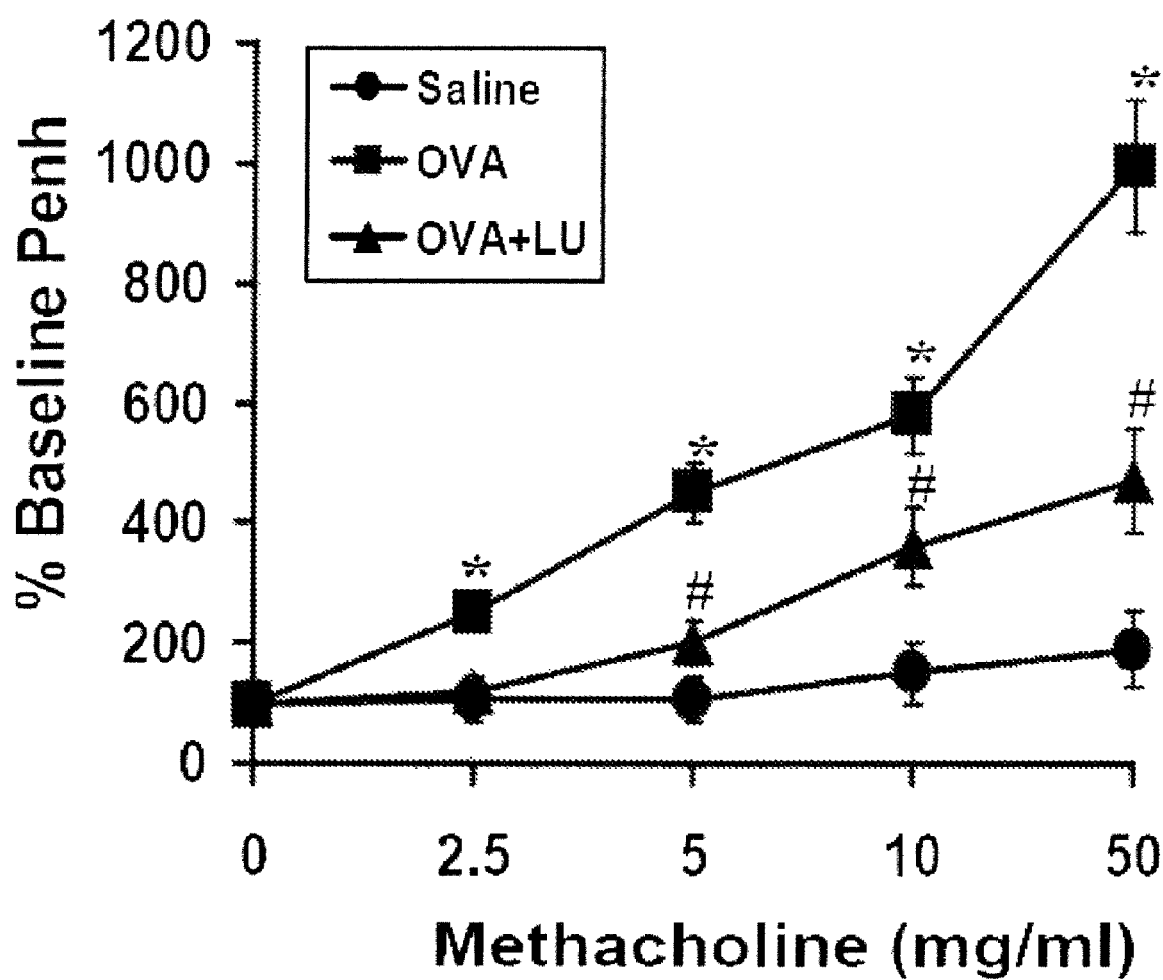
FIG. 4 illustrates the effect of an *L. undulata* extract (LU) on the airway responsiveness in OVA-sensitized and OVA-challenged mice.

In the OVA-sensitized and OVA-challenged mice, the dose-response curve of the percent Penh shifted to the left compared with that of the control mice (FIG. 4) (*$p<0.05$ vs. saline-treated mice; # $p<0.05$ vs. OVA-treated mice). In addition, the percent Penh produced by methacholine administration (at doses from 2.5 to 50 mg/ml) increased significantly in the OVA-sensitized and OVA-challenged mice compared with the controls. OVA-sensitized and OVA-challenged mice treated with LU showed a dose-response curve of the percent Penh that shifted to the right when compared to that of the control mice. The shift was dose-dependent. These results indicate that LU has an inhibitory effect on the OVA-induced airway hyperresponsiveness.

The Effect of LU on the Level of OVA-Specific Serum IgE

The level of OVA-specific serum IgE was determined by Enzyme Linked Immuno Sorbent Assay (ELISA) in the samples collected 12 h after the last OVA challenge. Blood was collected by cardiac puncture for measurement of OVA-specific IgE with ELISA. A 96 well microtitre plate was coated with OVA (10 mg/ml), and then treated with mouse sera followed by biotin-conjugated rat anti-mouse IgE (pharmingen, San Diego, Calif.). Then, avidin-horseradish peroxidase (HRP) solution was added to each well, and optical density was measured at 405 nm. Results were recorded as mean±S.E.M. from five separate experiments (n=6 per group).

Figure 5:
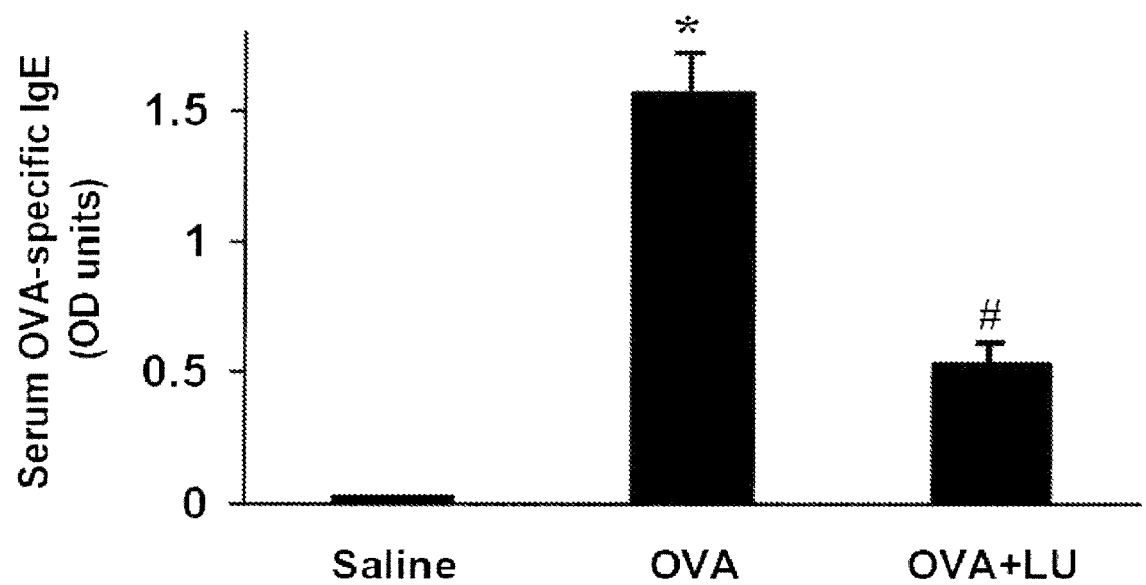
FIG. 5 demonstrates the effect of an *L. undulata* extract (LU) on the level of serum OVA-specific IgE.

Sensitization and challenge with OVA increased the serum level of OVA-specific IgE when compared with the saline-treated mice. Treatment of sensitized mice with LU resulted in a 66.05% reduction in OVA-specific IgE (FIG. 5, *$p<0.05$ vs. saline-treated mice; # $p<0.05$ vs. OVA-treated mice). The above data showed that the serum level of OVA-specific IgE was significantly reduced by LU pretreatment. These results indicate that LU suppressed the generation of a Th2-type immune response and the activity of mast cells.

Effects from Practicing the Present Invention

As can be seen from the above, an extract of *Laurencia undulata* according to the present invention can be effectively used for treating allergic diseases such as allergic rhinitis, atopic dermatitis, anaphylaxis, and asthma, especially, for treating asthma.

While the present invention has been shown and described with respect to the preferred embodiments, it will be understood by those skilled in the art that various changes and modifications may be made without departing from the spirit and the scope of the present invention as defined in the following claims.

What is claimed is:

1. A method of treating atopic dermatitis, the method comprising:
administering an alcohol-based extract of *Laurencia undulata* in a therapeutically effective amount to a patient in need thereof, wherein the alcohol-based extract of *Laurencia undulata* decreases levels of eosinophil in the bronchoalveolar lavage fluid of the patient and treats atopic dermatitis in the patient.

2. The method according to claim 1, wherein said alcohol-based extract is extracted with an alcohol solution of 40% to 99%.

3. The method according to claim 2, wherein said alcohol-based extract is extracted with 95% ethanol.

4. The method according to claim 1, wherein said alcohol-based extract is prepared by lyophilizing and homogenizing *Laurencia undulata* followed by extracting with 95% ethanol in a weight/volume ratio of 1:10, wherein the weight/volume indicates weight of dried *Laurencia undulata*/volume of 95% ethanol.

5. The method according to claim 1, wherein the therapeutically effective amount is a daily dose of an amount from approximately 0.1 g to approximately 100 g.

6. The method according to claim 1, wherein the alcohol-based extract of *Laurencia undulata* decreases the levels of IL-4, IL-5 and TNF-α in the bronchoalveolar lavage fluid of the patient and treats atopic dermatitis in the patient.

7. The method according to claim 1, wherein the alcohol-based extract of *Laurencia undulata* decreases the levels of the concentration of serum IgE in the patient and treats atopic dermatitis in the patient.

8. The method according to claim 1, wherein the alcohol-based extract of *Laurencia undulate* comprises an ethanol extract of *Laurencia undulate*, a methanol extract of *Laurencia undulate*, a propanol extract of *Laurencia undulata*, and a butanol extract of *Laurencia undulate*.

9. A method of alleviating symptoms associated with atopic dermatitis, the method comprising:
administering an alcohol-based extract of *Laurencia undulata* in a therapeutically effective amount to a patient in need thereof, wherein the alcohol-based extract of *Laurencia undulata* decreases levels of eosinophil in the bronchoalveolar lavage fluid of the patient and alleviates symptoms associated with atopic dermatitis in the patient.

10. The method according to claim 9, wherein the therapeutically effective amount is a daily dose of an amount from approximately 0.1 g to approximately 100 g.

11. The method according to claim 9, wherein the alcohol-based extract of *Laurencia undulata* decreases the levels of IL-4, IL-5 and TNF-α in the bronchoalveolar lavage fluid of the patient and alleviates symptoms associated with atopic dermatitis in the patient.

12. The method according to claim 9, wherein the alcohol-based extract of *Laurencia undulata* decreases the levels of the concentration of serum IgE in the patient and alleviates symptoms associated with atopic dermatitis in the patient.

13. The method according to claim 9, wherein said alcohol-based extract is extracted with an alcohol solution of 40% to 99%.

14. The method according to claim 13, wherein said alcohol-based extract is extracted with 95% ethanol.

15. The method according to claim 9, wherein said alcohol-based extract is prepared by lyophilizing and homogenizing *Laurencia undulata* followed by extracting with 95% ethanol in a weight/volume ratio of 1:10, wherein the weight/volume indicates weight of dried *Laurencia undulata*/volume of 95% ethanol.

16. The method according to claim 9, wherein the alcohol-based extract of *Laurencia undulate* comprises an ethanol extract of *Laurencia undulate*, a methanol extract of *Laurencia undulate*, a propanol extract of *Laurencia undulate*, and a butanol extract of *Laurencia undulate*.

* * * * *